United States Patent [19]
Burke et al.

[11] Patent Number: 5,773,598
[45] Date of Patent: Jun. 30, 1998

[54] SYSTEMATIC EVOLUTION OF LIGANDS BY EXPONENTIAL ENRICHMENT: CHIMERIC SELEX

[75] Inventors: Donald Burke; Ted Tarasow; Bruce E. Eaton; Larry Gold, all of Boulder, Colo.

[73] Assignee: NeXstar Pharmaceuticals, Inc., Boulder, Colo.

[21] Appl. No.: 464,102

[22] Filed: Jun. 5, 1995

Related U.S. Application Data

[63] Continuation of Ser. No. 284,063, Aug. 2, 1994, Pat. No. 5,637,459, which is a continuation-in-part of Ser. No. 714, 131, Jun. 10, 1991, Pat. No. 5,475,096, which is a continuation-in-part of Ser. No. 536,428, Jun. 11, 1990, abandoned.

[51] Int. Cl.$^6$ .......................... C07H 21/02; C07H 21/04; C12P 19/34; C12Q 1/68
[52] U.S. Cl. ............................ 536/231; 536/254; 436/6; 436/91.2; 935/77; 935/78
[58] Field of Search ................................ 536/23.1, 25.4; 435/6, 91.1; 935/77, 78

[56] References Cited

U.S. PATENT DOCUMENTS 5,270,163  12/1993  Gold et al. .................................... 435/6

FOREIGN PATENT DOCUMENTS

| 2 183 661 | 6/1987 | United Kingdom . |
|---|---|---|
| WO 89/06694 | 7/1989 | WIPO . |
| WO91/19813 | 6/1991 | WIPO . |

OTHER PUBLICATIONS

Bartel et al. (1983) Science 261:141.
Beaudry et al. (1992) Science 257:635.
Gorman et al. (1982) Mol. Cell. Biol. 2:1044.
Irvine et al. (1991), J. Mol. Biol. 222:739.
Kiatmura et al. (1984) J. Am. Chem. Soc. 106:3252.
Piccirilli et al. (1990) Nature 343:33.
Schaumberg et al. (1985) J. Org. Chem. 50:1651.
Tuerk et al. (1990) Science 249:505.
Joyce (1989) Gene 82:83.
Joyce and Inoue (1989) Nucleic Acids Research 17:711.
Ellington and Szostak (1990) Abstract of papers presented at the 1990 meeting on RNA Processing, Cold Spring Harbor Laboratory, Cold Spring Harbor, NY, p. 226.
Kinzler and Vogelstein (1989) Nucleic Acids Research 17:3645.
Kramer et al. (1974) J. Mol. Biol. 89:719.
Levisohn and Spiegelman (1969) Proc. Natl. Acad. Sci. USA 63:805.
Levisohn and Spiegelman (1968) Proc. Natl. Acad. Sci. USA 60:866.
Oliphant et al. (1989) Mol. Cell. Biol. 9:2944.
Oliphant and Struhl (1988) Nucleic Acids Research 16:7673.
Oliphant and Struhl (1987) Methods in Enzymology 155:568.
Oliphant et al. (1986) Gene 44:177.
Robertson and Joyce (1990) Nature 344:467.
Thiesen and Bach (1990) Nucleic Acids Research 18:3203.
Frohman et al., PNAS 85:8998–9002 (Dec. 1988).
Mullis et al., CSHS Quant. Biol. LI:263–273 (1986).

Primary Examiner—Stephanie W. Zitomer
Attorney, Agent, or Firm—Swanson & Bratschun LLC

[57] ABSTRACT

Methods are disclosed for producing chimeric nucleic acid molecules with two or more functionalities. A chimeric library is generated in which individual chimeric molecules combine the functions or characteristics of two or more parent libraries, each parent library having been selected through the SELEX procedure for a specific function or feature. The chimeric molecules of this invention are useful in a variety of ways, including having improved affinities for a target molecule, enhancing assembly of multi-component molecules, and promoting reactions between two molecules.

5 Claims, 3 Drawing Sheets

SYSTEMATIC EVOLUTION OF LIGANDS BY EXPONENTIAL ENRICHMENT: CHIMERIC SELEX

RELATED APPLICATIONS

This application is a Continuation of U.S. patent application Ser. No. 08/284,063, filed Aug. 2, 1994, now U.S. Pat. No. 5,637,458, entitled Systematic Evolution of Ligands by Exponential Enrichment: Chimeric Selex. U.S. patent application Ser. No. 08/284,063 is a Continuation-in-Part of U.S. patent application Ser. No. 07/714,131, filed Jun. 10, 1991, entitled Nucleic Acid Ligands now issued as U.S. Pat. No. 5,475,096, which was a Continuation-in-Part of U.S. patent application Ser. No. 07/536,428, filed Jun. 11, 1990, entitled Systematic Evolution of Ligands by Exponential Enrichment, now abandoned.

This work was partially supported by grant No. CHE-9302453 from the United States Government funded through the National Foundation of Science. The U.S. Government may have certain rights in this invention.

FIELD OF THE INVENTION

Described herein are methods for generating chimeric nucleic acid molecules with multiple functionalities. The methods disclosed herein are based on the SELEX method for generating high affinity nucleic acid ligands. SELEX is an acronym for Systematic Evolution of Ligands by EXponential enrichment. The methods of this invention combine populations of nucleic acid molecules selected for specific functions to generate a chimeric nucleic acid molecule with multiple functionalities. The chimeric nucleic acid molecules of the invention may contain two or more high affinity binding domains for different target molecules or to different epitopes of the same target molecule. These chimeric molecules are useful in a variety of ways, including promoting assembly of multiple component molecules, promoting chemical or enzymatic reactivity between molecules, and as diagnostic and therapeutic agents.

BACKGROUND OF THE INVENTION

A method for the in vitro evolution of nucleic acid molecules with high affinity binding to target molecules has been developed. This method, Systematic Evolution of Ligands by EXponential enrichment, termed SELEX, is described in U.S. patent application Ser. No. 07/536,428, entitled Systematic Evolution of Ligands by EXponential Enrichment, now abandoned, U.S. patent application Ser. No. 07/714,131, filed Jun. 10, 1991, entitled Nucleic Acid Ligands now U.S. Pat. No. 5,475,096, U.S. patent application Ser. No. 07/931,473, filed Aug. 17, 1992, entitled Nucleic Acid Ligands, now U.S. Pat. No. 5,270,163 (see also WO91/19813), each of which is herein specifically incorporated by reference. Each of these applications, collectively referred to herein as the SELEX Patent Applications, describe a fundamentally novel method for making a nucleic acid ligand to any desired target molecule.

The SELEX method involves selection from a mixture of candidate oligonucleotides and step-wise iterations of binding, partitioning and amplification, using the same general selection theme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield high affinity nucleic acid ligands to the target molecule.

The basic SELEX method may be modified to achieve specific objectives. For example, U.S. patent application Ser. No. 07/960,093, filed Oct. 14, 1992, entitled Method for Selecting Nucleic Acids on the Basis of Structure, describes the use of SELEX in conjunction with gel electrophoresis to select nucleic acid molecules with specific structural characteristics, such as bent DNA. U.S. patent application Ser. No. 08/123,935, filed Sep. 17, 1993, entitled Photoselection of Nucleic Acid Ligands, describes a SELEX based method for selecting nucleic acid ligands containing photoreactive groups capable of binding and/or photocrosslinking to and/or photoinactivating a target molecule. U.S. patent application Ser. No. 08/134,028, filed Oct. 7, 1993, entitled High-Affinity Nucleic Acid Ligands That Discriminate Between Theophylline and Caffeine, describes a method for identifying highly specific nucleic acid ligands able to discriminate between closely related molecules, termed "counter-SELEX". U.S. patent application Ser. No. 08/143, 564, filed Oct. 25, 1993, entitled Systematic Evolution of Ligands by EXponential Enrichment: Solution SELEX, describes a SELEX-based method which achieves highly efficient partitioning between oligonucleotides having high and low affinity for a target molecule.

The SELEX method encompasses the identification of high-affinity nucleic acid ligands containing modified nucleotides conferring improved characteristics on the ligand, such as improved in vivo stability or delivery. Examples of such modifications include chemical substitutions at the ribose and/or phosphate and/or base positions. Specific SELEX-identified nucleic acid ligands containing modified nucleotides are described in U.S. patent application Ser. No. 08/117,991, filed Sep. 8, 1993, entitled High Affinity Nucleic Acid Ligands Containing Modified Nucleotides, that describes oligonucleotides containing nucleotide derivatives chemically modified at the 5- and 2'-positions of pyrimidines, as well as specific RNA ligands to thrombin containing 2'-amino modifications. U.S. patent application Ser. No. 08/134,028, supra, describes highly specific nucleic acid ligands containing one or more nucleotides modified with 2'-amino (2'-$NH_2$), 2'-fluoro (2'-F), and/or 2'-O-methyl (2'-OMe).

The development of a method for generating chimeric nucleic acid molecules containing more than one functionality is desirable. Such molecules would combine multiple functionalities in a single molecule, and could be selectively designed to carry out a myriad of previously unknown unique activities.

BRIEF SUMMARY OF THE INVENTION

The present invention describes methods for generating chimeric nucleic acid molecules. Further included in this invention are chimeric nucleic acid libraries and chimeric nucleic acid molecules so generated. The chimeric nucleic acid molecules generated by the methods of this invention may perform in a number of unique ways. For example, chimeric nucleic acid molecules with two high affinity binding domains to a single target molecule may achieve higher binding affinities than possible with a single binding domain. Chimeric nucleic acid molecules may function to assemble a multi-subunit molecule, or to catalyze a chemical reaction between two or more molecules.

In one embodiment of the method of this invention, a method for generating chimeric nucleic acid molecules is described, comprising:

a) generating a first library of nucleic acids selected through the SELEX procedure for a first function, said nucleic acids having a 3' fixed sequence;

b) generating a second library of nucleic acids selected through the SELEX procedure for a second function, said nucleic acids having a 5' fixed sequence identical to the 3' fixed sequence of the nucleic acids of said first library;

c) mixing said first and second libraries under conditions which promote interlibrary annealing;

d) forming chimeric nucleic acid molecules by enzymatically extending the recessed 3' ends while copying the 5' extensions of each annealed pair; and e) amplifying said chimeric nucleic acid molecules to generate double-stranded DNA.

In embodiments of the invention where a single-stranded RNA chimeric library is desired, the method further comprises the step:

f) transcription of said double-stranded DNA to yield a single-stranded RNA chimeric nucleic acid library.

In embodiments of the invention where a single-stranded DNA library is desired, the method further comprises the step:

f) separating the strands of said double-stranded DNA to yield a single-stranded DNA chimeric nucleic acid library.

In a second embodiment of the method of this invention, a method is described for generating chimeric nucleic acid molecules, comprising:

a) generating a first library of nucleic acids selected through the SELEX procedure for a first function, said nucleic acids having a monophosphate at the 5' end;

b) generating a second library of nucleic acids selected through the SELEX procedure for a second function; and c) mixing said first and second libraries under conditions where the nucleic acids of the first library are enzymatically or chemically joined to the nucleic acids of the second library to form chimeric nucleic acid molecules, to yield said chimeric nucleic acid library.

A further embodiment of the method of the present invention involves the generation of a chimeric nucleic acid library that is comprised of nucleic acid sequences each having at least two nucleic acid domains that are linked to each other via their 3' ends. Use of such a library allows for the identification of chimeric nucleic acid molecules having at least two functional nucleic acid domains linked at the 3' end of each nucleic acid. Such chimeric nucleic acid molecules would not be susceptible to endonucleases that rely on 3' to 5'degradation, and would therefore yield desirable in vivo therapeutic and diagnostic agents.

The method of this embodiment of the invention comprises the preparation of a library of nucleic acid sequences, each of which is chemically modified at the 3'end so that the sequences may be randomly dimerized to form the 3'—3'-linked chimeric nucleic acid library. Such library may be then used in the SELEX process. The two separate domains of the selected chimeric nucleic acid molecules can be separated prior to amplification. Alternatively, the two domains can be amplified separately from a dimer template by design of the amplification experiment. This embodiment of the invention generates nucleic acid domains that are selected for in the chimeric nucleic acid dimeric library. Subsequent rounds of SELEX first require dimerization of the selected and amplified nucleic acid sequences from the previous round of SELEX.

This invention includes the chimeric library of nucleic acid molecules generated by the methods of the invention comprised of nucleic acids with functionalities contributed by each of a plurality of parent libraries.

This invention further includes the chimeric nucleic acid molecules generated by the methods of this invention. These chimeric nucleic acid molecules may contain one or more modified nucleotides such as nucleotides modified at the 5-, 2'- and/or 5' positions. Such modifications include but are not limited to nucleotides containing 2' amino (2'-NH$_2$), 2' fluoro (2'-F), and 2'-O-methyl (2'-OMe) groups.

The invention still further includes the use of the chimeric nucleic acid molecules of this invention to is generate or identify other nucleic acid molecules.

BRIEF DESCRIPTION OF THE FIGURES

FIG. 1 illustrates the chimeric SELEX method of the present invention formed from libraries A and B. (a) Double-stranded DNA is generated from each library. (b) The two libraries A and B are mixed, denatured, and allowed to anneal. (c) The overlap in sequence between the libraries' fixed regions allows for substantial interlibrary annealing, leaving 5' extensions that are enzymatically copied. (d) Amplification of the resulting chimeric nucleic acid molecules generates a chimeric nucleic acid library (AB) that combines the domains responsible for the separate activities or functions of each library into a single molecule. A and B are populations of nucleic acids selected for functions A and B. X, Y and Z are segments of fixed sequence, with complements X', Y' and Z'. The dark regions on the left-hand sides are promoters.

FIG. 2 illustrates two alternate methods of fusing two libraries (A and B) to form a chimeric nucleic acid library. In FIG. 2B monophosphate is placed at the 5' end of only one of the libraries and the two libraries joined by enzymatic ligation. A and B are populations of nucleic acids selected for functions A and B. W, X, Y and Z are segments of fixed sequence, with complements W', X', Y' and Z'. Y1 and Y2 and Y1' and Y2' are subsegments of Y and Y', interrupted by a random region ("n") of length n. n' is the complement of n. The dark regions on the left-hand sides are promoters. P is a phosphate.

DETAILED DESCRIPTION OF THE INVENTION

This application describes methods for generating chimeric nucleic acid molecules. Examples of chimeric nucleic acid libraries and molecules generated by these methods are provided. The methods herein described are based on the SELEX method. SELEX is described in U.S. patent application Ser. No. 07/536,428, entitled Systematic Evolution of Ligands by EXponential Enrichment, now abandoned, U.S. patent application Ser. No. 07/714,131, filed Jun. 10, 1991, entitled Nucleic Acid Ligands, now U.S. Pat. No. 5,475,096, U.S. patent application Ser. No. 07/931,473, filed Aug. 17, 1992, entitled Nucleic Acid Ligands, now U.S. Pat. No. 5,270,163 (see also WO91/19813). These applications, each specifically incorporated herein by reference, are collectively called the SELEX Patent Applications.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: a) to assist in the amplification steps described below; b) to mimic a sequence known to bind to the target; or c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, each successively formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for the preparation of the initial candidate mixture; methods for partitioning nucleic acids within a candidate mixture; and methods for amplifying partitioned nucleic acids to generate enriched candidate mixtures. The SELEX Patent Applications also describe ligand solutions obtained to a number of target species, including protein targets wherein the natural role of the protein is and is not a nucleic acid binding protein. In co-pending and commonly assigned U.S. patent application Ser. No. 07/964,624, filed Oct. 21, 1992, now U.S. Pat. No. 5,496,938 (the '938 Patent), methods are described for obtaining improved nucleic acid ligands after SELEX has been performed. The '938 Patent, entitled Nucleic Acid Ligands to HIV-RT and HIV-1 Rev, is specifically incorporated herein by reference.

The present invention describes methods for generating nucleic acid molecules with more than one function. These methods are herein referred to as "chimeric SELEX". The conventional SELEX method generates nucleic acid libraries—or candidate mixtures—evolved for a particular function, such as affinity for a target molecule.

Carried to its extreme, conventional SELEX identifies nucleic acids with a specifically desired function. Conventional SELEX evolved libraries that are composed of ligands that have an increased affinity to a target, and/or specific nucleic acid ligands identified via SELEX, are used in the chimeric SELEX method for the generation of chimeric nucleic acid molecules. The chimeric SELEX methods combine two or more SELEX-evolved nucleic acid ligands and/or nucleic acid libraries (often referred to herein as parent libraries) into a single chimeric nucleic acid molecule containing the functions of both parent libraries and/or nucleic acid ligands. The chimeric SELEX methods of the present invention generate a single chimeric nucleic acid library from two or more independently identified parent libraries.

The chimeric nucleic acid libraries generated by the method of this invention may serve as candidate mixtures for further evolution through the SELEX procedure, or they may simply be partitioned for identification of chimeric nucleic acid molecules having the desired characteristics. The methods presented herein for generation of a chimeric nucleic acid library allow for exhaustively combining every individual nucleic acid member of each library with nucleic acids from a second library to form the chimeric nucleic acid molecules of the invention.

Utilizing standard SELEX procedures as disclosed in the SELEX Patent Applications, the number of rounds of SELEX performed in order to evolve a homogenous candidate mixture or a candidate mixture where all members have a high affinity for the target varies upon many conditions, including the nature of the target, the desired affinity, and binding conditions. Generally, after about 2–10 rounds of SELEX the resultant candidate mixture is only partially resolved, although highly enriched in nucleic acid sequences with the desired function. Generally, only after greater than 10 rounds of SELEX does the candidate mixture become highly resolved.

A chimeric nucleic acid molecule is defined as a nucleic acid molecule generated from two or more nucleic acid libraries and comprised of functions derived from the parent libraries. In the preferred embodiment of the invention, at least one of the nucleic acid libraries utilized as a parent library is obtained by the SELEX process. These chimeric nucleic acid molecules may contain one or more modified nucleotides such as nucleotides modified at the ribose and/or phosphate and/or base positions, including modification at the 5-, 2'- and/or 5' positions. Such modifications include but are not limited to nucleotides containing 2'-amino (2'-NH$_2$), 2'-fluoro (2'-F), and 2'-O-methyl (2'-OMe) groups.

A chimeric nucleic acid library is defined as a collection of nucleic acids, each nucleic acid comprised of at least two nucleic acid domains. Each nucleic acid domain is derived from a separate parent nucleic acid library. The parent libraries are preferably comprised of nucleic acids generated following at least one round of SELEX and is enriched in nucleic acids for a chosen function. Each member of the chimeric nucleic acid library may also be composed of fixed regions. Fixed regions are nucleic acid regions that are the same, or fixed, for each member of the chimeric nucleic acid library. Each member of the chimeric nucleic acid library may also contain linker regions. Linker regions are non-nucleic acid chemical units that couple nucleic acid domains of each member of the chimeric nucleic acid library.

Figure 1:
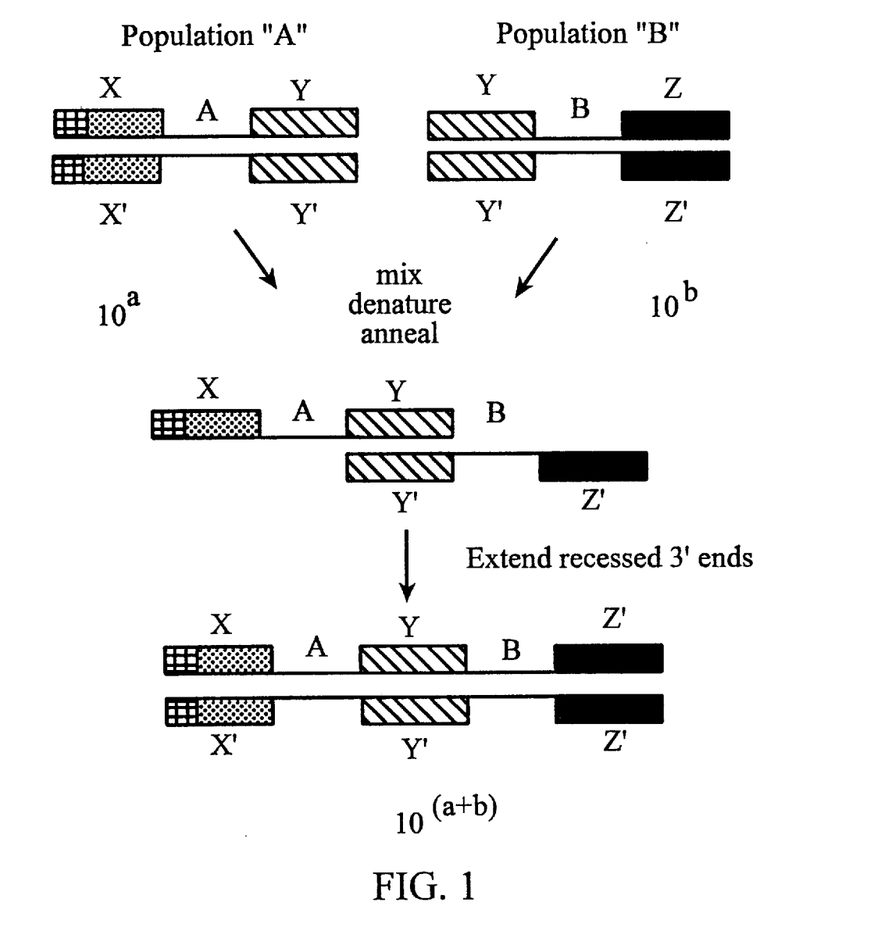

In one embodiment of the method of this invention, a chimeric nucleic acid library is generated by an overlap-extension reaction. Typically, the number of unique nucleic acids in a SELEX-derived library that has been selected for a given function is very small in comparison with the initial random population from which it was selected. Two such libraries serve as parent libraries for deriving the chimeric nucleic acid library. According to this embodiment, each nucleic acid sequence in both parent libraries is designed to contain a fixed region sequence at each end. For example, a portion of the 3' fixed region of library A is identical in sequence to the 5' fixed region of library B. These common fixed regions may be present in the initial candidate mixtures used to generate the parent SELEX-derived libraries, or may be added at a subsequent step. Double-stranded DNA is then generated from each library, mixed together, denatured, and allowed to anneal (FIG. 1). The overlap in sequence between the two libraries' fixed regions allows substantial interlibrary annealing, leaving 5' extensions that can be copied enzymatically. Amplification of the resulting chimeric nucleic acid molecules generates a new library of nucleic acids that combine two high affinity domains into each chimeric nucleic acid molecule (FIG. 1). The chimeric molecules generated by the methods of this invention may be further combined with other libraries to form more complex molecules with a wider array of functionalities.

Figure 2A:
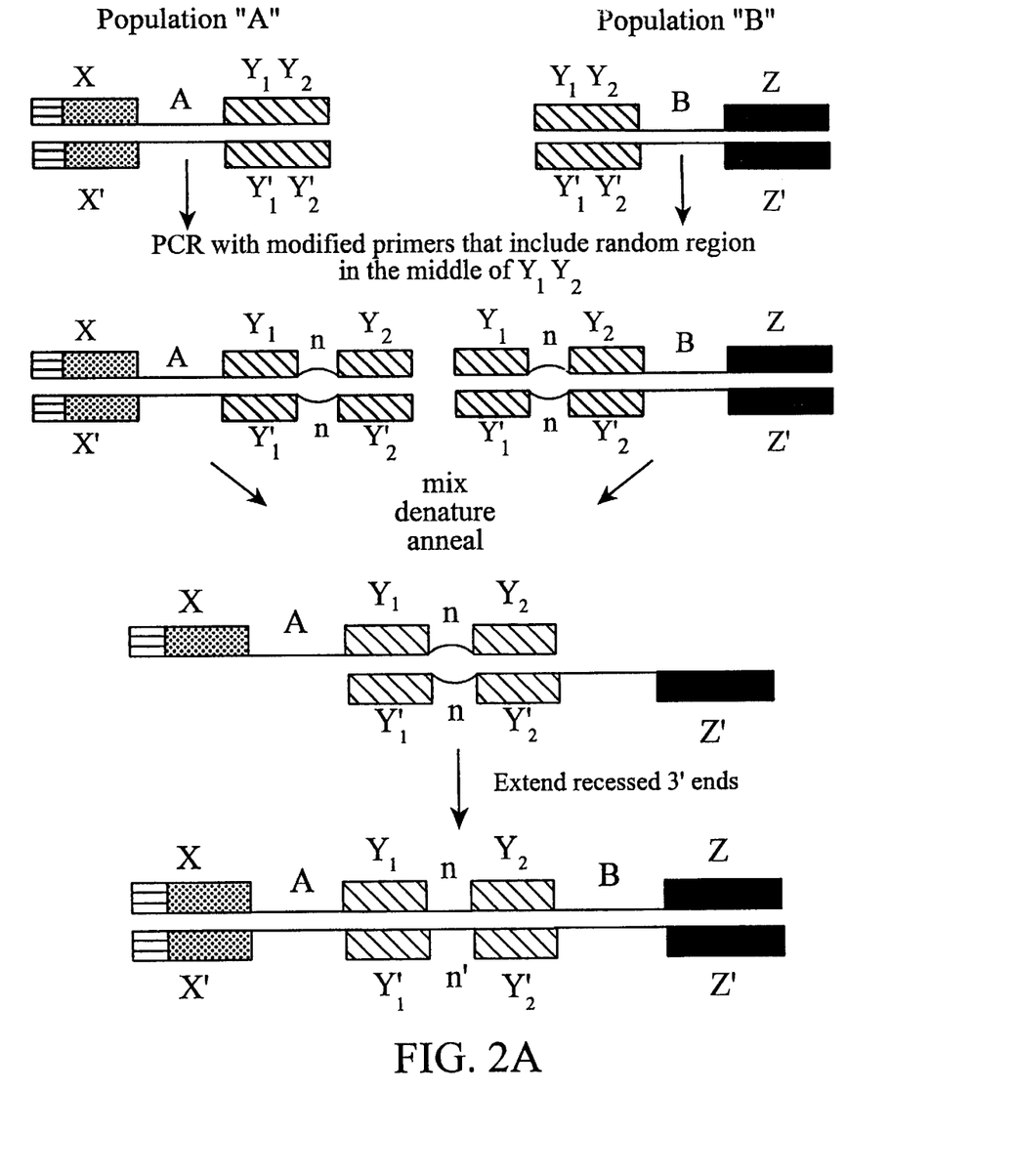
In FIG. 2A libraries A and B are amplified using primers that contain nucleotides of either random or defined sequence within their central regions. These amplified libraries are then combined as in FIG. 1.
Figure 2B:
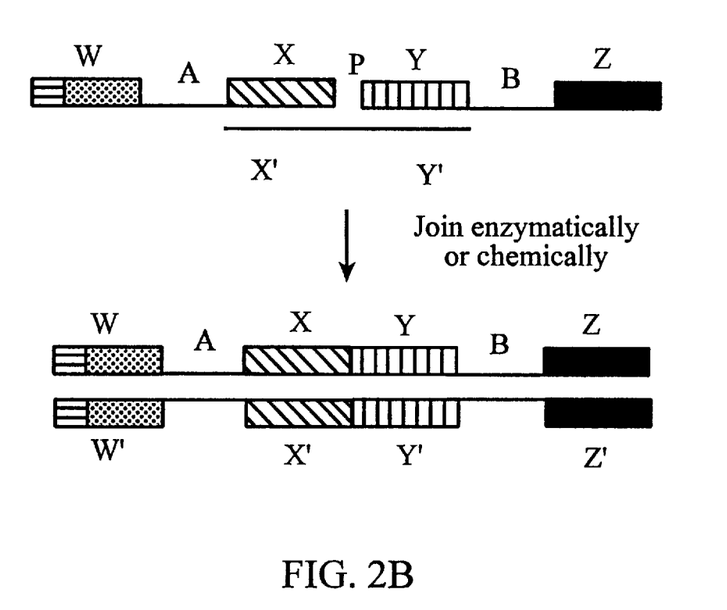

Fusion of the elements to form the chimeric nucleic acid library is described above as involving overlap extension at the level of double-stranded DNA; however, other methods of fusion can also be envisioned. In a second embodiment of the method of this invention, a chimeric nucleic acid library is generated by placing a monophosphate at the 5'-end of only one of the two parent nucleic acid libraries and members of the two parent libraries are joined by enzymatic ligation (FIG. 2). The 5'-monophosphate may be generated in a number of ways, including by restriction digestion, kinasing, or by priming transcription with a nucleotide monophosphate.

Further methods of fusion between nucleic acid members of the parent libraries may be used in the generation of a chimeric nucleic acid library. For example, prior to the chimeric fusion, one of the two parent nucleic acid libraries may be amplified using a primer that contains within its central region a number of random nucleotides. In such an embodiment, the link between the two nucleic acid portions responsible for the first and second functionalities would not be fixed. This allows introduction of variability and increased diversity to the new chimeric nucleic acid library.

An additional embodiment of the present invention includes a method for the production of chimeric 3'—3'-linked nucleic acid libraries and the further identification of chimeric 3'—3'-linked nucleic acid molecules. According to this embodiment of the invention, SELEX is performed on a chimeric 3'—3'-linked nucleic acid domain library.

A parent library of single stranded nucleic acid sequences comprised of at least one randomized or partially randomized domain is prepared according to standard SELEX procedures. Such library is "dimerized" by the use of chemical linkers at the 3' residues of each member of the parent library. After purification, the chimeric 3'—3'-linked nucleic acid library—comprised of 3'—3'-linked heterodimers—is used as a candidate mixture for SELEX. Following partitioning, the selected members of the chimeric candidate mixture are amplified to yield monomers, representing each half of the selected chimeric dimers. 3'—3'-linking or dimerization is again performed, and subsequent rounds of SELEX performed.

According to this SELEX method, early rounds of SELEX will identify chimeric 3'-linked dimers where only one of the nucleic acid domains has an increased affinity to the target. Once the library is enriched to the point that many "halves" of the chimeric dimers have affinity to the target, the $K_d$ will drop as heterodimers are formed that are comprised of more than one nucleic acid domain that have a high affinity for the target. These chimeric 3'—3'-linked diners will not stay together during the amplification step of SELEX, so particular dimers will not be identified.

This method for performing SELEX is particularly advantageous for circumstances where SELEX is conducted in vivo or where the target mixture may contain nucleases that degrade nucleic acids not capped at the 3' end.

The linkage of nucleic acids may be accomplished via a variety of applicable chemical schemes that would be available to one skilled in the art. An exemplative procedure for the 3'—3'-linking of two oligonucleotides whose 3'-terminus consists of a ribonucleotide can be achieved with a bifunctional linker in two successive chemical reaction steps. One such scheme is shown below:

According to this reaction scheme, a bifunctional diol-specific linker can be assembled from 4-hydroxybenzaldehyde dimethylacetal and phenyltrichlorosilane to give the corresponding dichloro phenyl-O-(4-dimethoxymethylphenyl)-siloxane. This siloxane linker can react with the 3' diol end of an oligoribonucleotide in acetonitrile in the presence of triethylamine and hydroxybenzotriazole to give the 2',3'-siloxane modified oligonucleotide. Schaumberg et al. (1985) J. Org. Chem. 50:1651. Activation with pyridinium para-toluenesulfonate enables reaction of the acetol end of the linker with the 3'-diol terminus of a second oligonucleotide. Kitamura et al. (1984) J. Am. Chem. Soc. 106:3252.

Obviously, the linker design need not be heterobifunctional. A homobifunctional linker with two acetal moieties, for instance, works analogously. In such a case, linking of two oligonucleotides proceeds in one reaction step. The linker may further bear substituents that constitute desired functional groups, such as detectable moieties. It can also bear a reactive functional group suitable for further chemical modification of the linker. A trifunctional linker entity is also possible with analogous chemistry.

An additional chemical scheme for the 3'—3'-linking of oligonucleotides is based on the discovery that 2',3'-isopropylidene adenosine is very stable and that the isopropylidene cannot be removed even under strong aqueous acid conditions.

A simple reaction scheme for the formation of 3'—3'-linkage of oligonucleotides can be accomplished simply by treating oligonucleotides according to the scheme shown below:

Y constitutes the spacer portion of the linker, and can be any of a wide variety of chemical constituents including branched or straight chain alkyls, natural or synthetic polymeric units such as polyethylene glycol, or any other chemical unit that can be attached to a plurality of aldehydes. An acid catalyst is used to facilitate the acetal linkage formation between the aldehyde functionality and the 2' and 3' cis hydroxyls of the oligonucleotide. The chemistry is very mild and selective for cis vicinal hydroxyls so that other functional groups on the RNA will not be affected.

A procedure for attaching different oligonucleotides or oligonucleotides from different libraries may be accomplished via the following chemical procedure:

According to this scheme, (where the spacer Y is depicted as a straight chain alkyl) a first oligonucleotide reacts with a linker that is comprised of an aldehyde and a carboxylic acid. Following the first linkage, the carboxylate is converted to the amide by treating with excess diamine and a condensation reagent. The primary amino group is then reacted with a second oligonucleotide that has already been reacted with an aldehyde/acid linker, to form the amide and create the 3'—3'-linked heteromer.

The present invention includes the above methods for 3'—3' linking of nucleic acid sequences, as well as chimeric nucleic acid libraries incorporating such 3'—3'-linkages, and individual chimeric nucleic acid sequences incorporating such 3'—3'-linkages. In its broadest sense, the invention includes all compounds comprised of the formula:

wherein B is any of the natural nucleic acid bases or any modified nucleic acid bases, n is any number greater than 1 and Y is any spacer, as described above.

The methods of this invention present several novel and important advantages over the prior art. For example, previous methods generating nucleic acid ligands to a target molecule were generally not known to contain a second, dissimilar functionality or feature, or ability to perform a second dissimilar task. "Functionality" or "feature" is defined as a specific trait present in an nucleic acid selected through the SELEX procedure. Functions and features include, for example, the ability to bind a target molecule, inhibition or enhancement of the biological activity of a target molecule and/or ability to catalyze a reaction. "Tasks" are hereby defined as the ability to perform a function such as binding to a specific molecule or epitope of a target molecule, ability to catalyze a chemical reaction or promote a reaction between two or more molecules, promoting the assembly of a multi-component molecule, or any other activity which the nucleic acid may be found to perform. The chimeric molecules produced by the methods of this invention uniquely combine two or more functionalities into a single molecule.

Further, a chimeric nucleic acid library may be used to restore non-arbitrary diversity to a candidate mixture for use in future SELEX experiments. The chimeric nucleic acid library achieves this by combining all the members of a selected population specifically with all of the members of another selected population. The spacer region between the two selected domains may also be allowed to vary, both in length and in sequence, thereby introducing another source of diversity. This is true whether or not additional variability is introduced into members of the parent libraries during the combinatorial step.

The chimeric nucleic acid molecules of this invention are utilizable in a number of unique ways. For example, in one embodiment of the method of the invention, different molecules may be selected through the SELEX procedure for high affinity binding to different epitopes of the same target molecule. These two ligands may be combined through the method of the present invention to form a single chimeric ligand (Example 1). When exposed to the target molecule, one of the two domains of the chimeric nucleic acid molecule binds to the target molecule. The binding of the second domain to the target molecule may occur with a very low entropy cost. Therefore, the overall binding may be greatly enhanced. Typical dissociation constants (Kd) for SELEX-identified RNA ligands are in the order of 1–100 nM (see, for example, U.S. patent application Ser. Nos. 07/973,333, filed Nov. 6, 1992, entitled Ligands of Thrombin, now U.S. Pat. No. 5,476,766; 08/061,691, filed Apr. 22, 1993, entitled Ligands of bFGF; 08/134,028, filed Oct. 7, 1993, entitled High-Affinity Nucleic Acid Ligands That Discriminate Between Theophylline and Caffeine). By combining two ligands into the same molecule and selecting for binding of even higher affinity, chimeric ligands with dissociation constants in the order of pM—fM may be obtained.

In another embodiment of the method of the invention, two nucleic acid molecules are selected with high affinity to epitopes on two subunits of the same multi-subunit macromolecule (Example 2). Selected chimeric nucleic acid ligands bind the assembled multi-subunit complex very tightly, or may even function to force its assembly by bringing the subunits together.

In one embodiment of the method of the invention, a chimeric nucleic acid molecule is selected which promotes enhanced catalysis between two components (Example 3). For example, two high affinity nucleic acid libraries are generated through SELEX to two molecules, which normally react slowly or without sufficient regiospecificity. Each of the parent libraries is prepared by performing SELEX for enough rounds to generate a mixture of ligands highly enriched for nucleic acid sequences that have higher affinity for one of the components. From the two parent libraries, a chimeric nucleic acid library may be prepared to provide a source of chimeric nucleic acid molecules. Chimeric nucleic acid ligands which bind both molecules are then generated by the method of this invention. Chimeric nucleic acid ligands are then screened to identify those molecules which promote faster or more regiospecific reactivity between the two molecules.

It is generally difficult to identify catalytic nucleic acid ligands by in vivo selection. This results from the difficulty of generating enough independent transformants to compensate for the infrequency of molecules with the desired selectable phenotype, such that the desired molecule may not be present in the transformed set. At present, obtaining more than $10^6$ independent transformants represents a major technological challenge, whereas the frequency of molecules that bind to a given target in a random population of candidate molecules is typically $10^{-8}$ to $10^{-12}$. For two dissimilar targets, the number of molecules able to bind both may be on the order of $10^{-20}$. There are insufficient data to know how additionally restrictive it would be to ask such molecules to catalyze a reaction, but it is likely to be only a small fraction of those molecules able to bind both substrates. Therefore, only by generating a large number of different molecules, all of which bind both substrates, will the fraction of molecules able to catalyze a reaction between two substrates be within reach of in vivo selection techniques.

In place of screening chimeric nucleic acids for catalytic activity individually, direct selection for such catalysts may be employed, either in vivo or in vitro. In the case of in vivo selection, those skilled in the art may design systems where survival of the host cell is dependent upon the presence of an expressed RNA from the chimeric nucleic acid populations, whereas in the case of in vitro selection, systems may be designed where those nucleic acids that can convert a covalently attached substrate into product are partitioned from those that cannot, either during or before the amplification step.

A similar method may be used to generate a chimeric nucleic acid ligand library with high affinity to two molecules. The chimeric molecules would then be selected for ability to catalyze the reaction of the two molecules to produce a third molecule (Example 4). Prior to or during amplification, those chimeric nucleic acid molecules that can be shown to be associated with the production of the third molecule are partitioned from those that do not. Therefore, this strategy incorporates a direct selection for a desired third activity such as catalysis.

The method of the present invention envisions the generation of chimeric nucleic acid molecules with special functions. For example, in one embodiment, a first parent library of nucleic acids is comprised of conventional ribozymes engineered and selected to cleave the single-stranded RNA genome of a retrovirus near the binding site for some sequence-specific protein "X". A second parent library is selected for high affinity binding to protein "X". The chimeric nucleic acid molecules produced by the method of this invention are able to deliver the ribozyme to the site at which it is intended to cleave the genome (Example 5).

The present invention encompasses chimeric nucleic acid molecules with two or more functionalities. For example, further chimeric nucleic acid molecules may be produced which introduce a third functionality to one of the dual functional chimeric nucleic acid molecules described above (Example 6).

The special attributes of the parent nucleic acid libraries used to generate chimeric nucleic acid molecules are not limited. The breadth of illustrative examples given above provides indication that the application of chimeric nucleic acid libraries is at least as broad as those of the SELEX method. One or more parent libraries may be selected to perform a specific task or impart a chemical component not carried by the first. For example, the genetic code has been expanded to include a novel base pair which is distinct from the canonical nucleotides A, G, C, T and U (Piccirilli et al. (1990) Nature 343:33). This base pair is fully compatible with the SELEX technologies and may be incorporated into one or both of the two domains of the chimeric nucleic acid molecules if desired. Additionally, modified nucleotides, including 5-pyr, 2'-fluoro, 2'-amino, and 2'-O-methyl, may be substituted for conventional nucleotides either in the generation of the parent libraries of nucleic acids or subsequent to their fusion.

According to one embodiment of the present invention, nucleic acids are 3'—3'-linked. In one embodiment the linkage occurs due to the selective reaction of an aldehyde or protected aldehyde with the 2',3' hydroxyl groups of the 3' terminal nucleic acid residue of an RNA. The inventors hereto have surprisingly discovered that the resultant acetals are extremely stable under a wide variety of conditions. The basic reaction conditions for the formation of such acetals are laid out in Example 7, which demonstrates the reaction by forming the acetal between guanosine 5'-monophosphate disodium salt (GMP) and benzaldehyde dimethyl acetal.

Specific examples of chimeric selection are herein provided. These examples are to illustrate and demonstrate the method of the invention, and are not intended to limit the scope, utility, or applicability of this invention.

EXAMPLE 1

Generation of Chimeric Nucleic Acid Molecules

Two nucleic acid libraries, A and B, were independently derived populations of ligands to the target protein HIV-1 Reverse Transcriptase (HIV RT). Detailed methods for generating libraries to HIV RT have been described (Tuerk and Gold (1990) Science 249:505). In brief, each cycle of selection/amplification involved 1) transcription of a double-stranded DNA template into RNA, and purification of the RNA transcript; 2) contacting the RNA with HIV RT; 3) binding the protein to a nitrocellulose filter and washing the filter to remove nonspecifically bound and free RNAs; 4) recovery of bound RNAs; and 5) reverse transcription of purified RNA into cDNA and amplification of cDNA into double-stranded DNA.

During the selection of each parent library, the bulk binding of the populations of RNA molecules became increasingly higher, as the RNA sequences unable to interact with HIV RT are eliminated from the population. If the SELEX procedure is carried out to its limit, only the highest affinity binding RNAs survive. Further, these RNA ligands may all bind the same site of the target protein. Therefore, in this embodiment of the method of the invention, each library was selected to the point where approximately $10^5$ to $10^6$ of the original $10^{14}$ random nucleic acids remained. The complexity of the nucleic acid library is calculated from the fraction of RNA that is retained on the filter in the presence and absence of protein (Irvine et al. (1991) J. Mol. Biol. 222:739)

Prior to the formation of chimeric nucleic acid molecules, double-stranded DNA was generated by PCR from each library in such a way that the 3' fixed sequence of library A is identical to the 5' fixed sequence of library B. Specifically, the 5' primer normally used to amplify library B was replaced by a primer that lacks sequences containing the transcriptional promoter. Amplified material from each library was gel purified, and the two libraries were mixed in an overlap-extension (OE) reaction.

Overlap-extension (OE) reaction. In OE, the DNA is denatured at high temperature and allowed to anneal for 10 min at 55° C. prior to extension at 72° C. with Taq DNA polymerase. This cycle is repeated 10 times to ensure that all the DNA from each library is extended. Then two primers, corresponding to the 5' fixed region of library A and the 3' fixed region of library B, are added and PCR performed to generate double-stranded DNA to be used as template for further cycles of selection/amplification. These additional cycles are carried out in the same manner as previous rounds of SELEX, except that much more stringent binding conditions may be used since some of the ligands contain binding domains for two separate epitopes of HIV RT.

EXAMPLE 2

Simultaneous Binding of Two Separate Molecules

Libraries A and B were independently derived populations of ligands for two distinct target molecules derived through standard SELEX methods. The target for library A was the antibiotic chloramphenicol (Cm), and the target for library B was Coenzyme A (CoA). The two libraries were generated as follows: purified RNA transcripts from a given library were denatured at 94° C. for 3 min in the absence of salts. A salt-containing buffer (Buffer 1: 50 mM Bis-Tris, pH 6.4, 200 mM NaCl, 10 mM $MgCl_2$) was added to the RNA and the mixture quick cooled to allow folding. The RNA was then passed over a column of Cm- or CoA- derivatized agarose (Sigma Chemical Co., St. Louis, Mo.) and washed with 10 column volumes of Buffer 1 to remove non-specifically adhered RNA. Specifically bound RNA was then eluted from the column with Buffer 2 (Buffer 1 plus 10 mM Cm or 75 mM CoA), and this RNA was amplified as described above. After 9 rounds of selection/amplification, the majority of the RNA bound to the column and was eluted specifically with the target molecule.

Libraries A and B were combined as described in Example 1. Those RNAs that continue to bind Cm after formation of the chimeric molecules are selected by three cycles of selection/amplification as described in this example above. Subsequently, those Cm-binding, chimeric molecules which continue to bind CoA are selected by three additional cycles of selection/amplification. All such selected chimeric nucleic acid molecules in the final chimeric nucleic acid library bind both CoA and Cm.

EXAMPLE 3

Nucleic Acid Based Catalysis

The chimeric library generated in Example 2 is screened for individual chimeric nucleic acid molecules capable of transferring an acetyl group from acetyl CoA to Cm.

Individual species are cloned from the chimeric nucleic acid library generated in Example 2. PCR of the plasmids from these clones is used to generate templates for transcription of the individual chimeric RNA molecules. Purified transcripts are then assayed for Cm acetyl transferase (CAT) activity by following the transfer of the $^{14}C$-labelled acetyl group of acetyl CoA to Cm. The product is detected by autoradiography of TLC-separated reaction mixtures (Gorman et al. (1982) Mol. Cell. Biol. 2:1044).

EXAMPLE 4

Nucleic Acid Catalysis to Form a Third Molecule

In vivo selection of catalysts. The chimeric nucleic acid library generated in Example 2 is spliced into an appropriate vector, which carries the gene for Ampicillin (Amp) resistance and can direct transcription of the inserted chimerae. Those skilled in the art can choose from a wide array of vectors that meet these criteria. The recombinant constructs are introduced into E. coli, and the cells are grown in the presence of Amp, but without Cm. The cells are then grown in the presence of Cm but without Amp. The only cells that grow are i) those that harbor plasmids coding for an RNA capable of CAT activity, and ii) those that harbor spontaneous chromosomal mutations conferring Cm resistance. Class ii) cells soon lose their plasmids, and therefore are not able to reproduce when Amp is later added to the growth medium. Further purification against spontaneously arising mutations is achieved by isolating bulk plasmids from all cells surviving the first selection, and using this collection of plasmids to retransform, followed by a second round of antibiotic treatments.

In vitro selection of catalysts: Library A is selected to bind a peptide fragment from the surface of collagenase. The target peptide fragment is first attached to a column matrix via the sulfhydryl groups of two cysteine residues added to the N-terminus of the peptide, and peptide-binding RNAs are selected by target-based elution, as described in Example 2. Library B is completely random in sequence, except for the fixed ends which conform to the specifications outlined in Example 1.

Libraries A and B are combined as described in Example 1. Chimeric RNA molecules from the resulting constructs are ligated to a DNA oligonucleotide that has been conjugated to the target peptide at its C-terminus. Following incubation in the presence of $Zn^{++}$ ions to promote cleavage of the peptide, the RNA-DNA-peptide fragment is reduced with dithiothreitol (DTT). Those molecules which retain two sulfhydryl groups at their 5' ends are partitioned from those molecules where the peptide has been cleaved, thereby detaching the RNA from the cysteine residues, by separation on a mercury polyacrylamide gel. The strong interaction of mercury with sulfur causes those species with sulfhydryl groups to migrate more slowly, while the RNA without sulfhydryl groups attached at the 5' end migrate more quickly through the gel.

EXAMPLE 5

Special-Function Chimeric Nucleic Acid Molecules

Several ribozymes have been engineered to cleave single-stranded RNA genomes of retroviruses such as HIV. These ribozymes contain, with their primary sequences, portions that bind to the target substrate through Watson-Crick base pairing, such that ribozyme-mediated cleavage of the target may be predetermined to occur at a specific site.

Library A is selected from oligonucleotides having fifty random nucleotides appended at the 5'-end of an engineered ribozyme, along with a suitable region of fixed sequence. The target cleavage site of this particular ribozyme is near the HIV-1 genome site which binds the tat protein (TAR). Library A is chemically synthesized as single-stranded DNA, which will subsequently be combined with a second library B, to form the chimeric AB library.

Upon cleavage of the target molecule by the library A molecules, the 3' portion of the target molecule is transferred to the 3' end of the ribozyme by phosphodiester exchange. This 3' substrate portion is used as a selectable marker, either by using it as a binding site for the primer used in the reverse transcription step, or by hybridizing this sequence to its immobilized complement in the partitioning step (Beaudry and Joyce (1992) Science 257:635–641; Bartel et al. (1993) Science 261:1411–1418).

Library B consists of RNA ligands to the tat protein. Methods for generating tat-binding RNA ligands are known (See, U.S. patent application Ser. No. 07/953,694, filed Sep. 29, 1992, entitled Ligands of the HIV-1 tat protein).

Libraries A and B are combined to form a chimeric library as described in Example 1. Transcripts from the resulting chimeric molecules are subjected to selection through the SELEX procedure to ensure the continued functioning of the two functional domains. Partitioning through filter binding ensures the continued presence of the tat-binding domain, while amplification-based selection ensures the presence of an active ribozyme domain able to cleave the target. After three rounds of SELEX for each individual function, the resulting chimeric nucleic acid molecules are screened for their ability to cleave the HIV-1 genome in the presence and absence of the tat protein.

EXAMPLE 6

Chimeric Nucleic Acid Molecules with Three or More Functionalities

The functional domains of three libraries may be combined into one chimeric molecule.

A chimeric AB molecule is formed as described in Example 1, having binding to two separate epitopes of HIV-1 reverse transcriptase. A non-amplifiable variant of AB is used as a competitive inhibitor in a selection for HIV-1 binding RNAs to generate library C. SELEX is carried out as outlined in Example 1. RNA ligands are selected which bind HIV-1 RT at a site other than that of the chimeric AB ligand. The 5' fixed sequence region of library C oligonucleotides is identical to the 3' fixed sequence of the molecules of library C so that library C ligands may be combined with chimeric AB molecules as described in Example 1 above to form chimeric ABC molecules. Further rounds of SELEX will result in identification of very high affinity chimeric ABC molecules having binding sites for three epitopes to the HIV-1 RT protein.

EXAMPLE 7

3'—3'-Linking of Nucleic Acid Sequence

The ability to link nucleic acid sequences via acetal formation at the 2',3' positions of the 3' terminal nucleic acid residue has been demonstrated by the following reaction:

50 mg (0.124 mmol) of guanosine 5'-monophosphate disodium salt (GMP) and 60 mg (0.316 mmol) of p-toluenesulfonic acid monohydrate (TsOH) were dissolved in 1 mL of freshly dried dimethyl sulfoxide (DMSO). To this was added 0.5 mL (3.33 mmol) of benzaldehyde dimethyl acetal and the reaction vessel was capped and heated to 50° C. with stirring. After 24 hours of heating the mixture was concentrated to 100 μL using a speed-vac set on medium heat. The remaining residue was treated with 320 μL of 1N NaOH and concentrated on the speed-vac again to give a slightly yellow solid. The GMP acetal was purified by HPLC using a Vydac 218TP1022 reverse phase column and a gradient elution of 0% to 10% acetonitrile/water over 10 minutes followed by 5 minutes of eluting with 10% acetonitrile/water. The product was collected and the solvent removed under reduced pressure to give 35 mg (57%) of a white solid.

We claim:

1. A chimeric nucleic acid ligand having high binding affinity for first and second target molecules identified according to a method comprising:
   a) preparing a chimeric nucleic acid ligand library generated according to a method comprising:
      i) generating a first library of nucleic acid ligands selected through the SELEX procedure for binding to said first target molecule, said nucleic acid ligands having a 3' fixed sequence, and producing the double-stranded form of said first library of nucleic acid ligands;
      ii) generating a second library of nucleic acid ligands selected through the SELEX procedure for binding to said second target molecule, said nucleic acid ligands having a 5' fixed sequence identical to the 3' fixed sequence of the nucleic acid ligands of said first library, and producing the double-stranded form of said second library of nucleic acid ligands;
      iii) mixing said first and second libraries under conditions which promote interlibrary annealing;
      iv) forming chimeric nucleic acid ligands by enzymatically extending the recessed 3' ends while copying the 5' extensions of each annealed pair to yield a double-stranded nucleic acid ligand library; and
      v) amplifying said double-stranded chimeric nucleic acid ligand library;
   b) contacting said amplified chimeric nucleic acid ligand library with said first and second target molecules, wherein chimeric nucleic acid ligands having an increased affinity to said first and second target molecules may be partitioned from the remainder of the chimeric nucleic acid ligand library;
   c) partitioning said increased affinity chimeric nucleic acid ligands from the remainder of said chimeric nucleic acid ligand library; and
   d) amplifying said increased affinity chimeric nucleic acid ligands to yield a mixture of chimeric nucleic acid ligands enriched in members which bind to said first and second target molecules, whereby a chimeric nucleic acid ligand having high binding affinity to said first and second target molecules is identified.

2. A chimeric nucleic acid ligand having high binding affinity for first and second target molecules identified according to a method comprising:
   a) preparing a chimeric nucleic acid ligand library generated according to a method comprising:
      i) generating a first library of nucleic acid ligands selected through the SELEX procedure which bind to said first target molecule, said nucleic acid ligands having a 3' fixed sequence and a 5'-monophosphate;
      ii) generating a second library of nucleic acid ligands selected through the SELEX procedure which bind to said second target molecule;
      iii) mixing said first and second libraries under conditions where said nucleic acid ligands of said first library are enzymatically or chemically joined to said nucleic acid ligands of said second library to form chimeric nucleic acid ligands; and
      iv) amplifying said chimeric nucleic acid ligands, to yield said chimeric nucleic acid ligand library;
   b) contacting said amplified chimeric nucleic acid ligand library with said first and second target molecules, wherein chimeric nucleic acid ligands having an increased affinity to said first and second target molecules may be partitioned from the remainder of the chimeric nucleic acid ligand library;
   c) partitioning said increased affinity chimeric nucleic acid ligands from the remainder of said chimeric nucleic acid ligand library; and
   d) amplifying said increased affinity chimeric nucleic acid ligands to yield a mixture of chimeric nucleic acid ligands enriched in members which bind to said first and second target molecules, whereby a chimeric nucleic acid ligand having high binding affinity to said first and second target molecules is identified.

3. A chimeric nucleic acid ligand comprising 3'—3' linked nucleic acid ligands, said chimeric nucleic acid having high binding affinity for a target molecule identified according to a method comprising:
   a) preparing a chimeric nucleic acid library generated according to a method comprising:
      i) generating a first library of nucleic acid ligands selected through the SELEX procedure for binding to said target molecule wherein each of said nucleic acid ligands is modified at the 3' end to facilitate linking of members of said first library with each other; and
      ii) chemically reacting members of said first library of nucleic acid ligands to form chimeric 3'—3'-linked nucleic acid ligands which comprise said chimeric nucleic acid library;
   b) contacting said chimeric nucleic acid ligand library with said target molecule, wherein chimeric 3'—3' linked nucleic acid ligands having an increased affinity to said target molecule may be partitioned from the remainder of the chimeric nucleic acid ligand library
   c) partitioning said increased affinity chimeric 3'—3' linked nucleic acid ligands from the remainder of said chimeric nucleic acid library;
   d) amplifying said increased affinity chimeric 3'—3' linked nucleic acid ligands to yield a mixture of nucleic acid ligands representing each half of said chimeric 3'—3' linked nucleic acid ligands, enriched in nucleic acid ligands having increased affinity to said target molecule; and
   e) chemically reacting said mixture of amplified increased affinity nucleic acid ligands to form increased affinity chimeric 3'—3'-linked nucleic acid ligands, whereby a chimeric nucleic acid ligand comprising 3'—3' linked nucleic acid ligands having high binding affinity to said target molecule is identified.

4. The chimeric nucleic acid molecule of claim 1 identified according to a method further comprising between step a)v) and step b), the step:
   vi) transcription of said double-stranded nucleic acid ligand library to yield a single-stranded RNA chimeric nucleic acid ligand library.

5. The chimeric nucleic acid molecule of claim 1 identified according to a method further comprising between step a)v) and step b), the step:
   vi) separating the strands of said double-stranded nucleic acid ligands to yield a single-stranded nucleic acid chimeric nucleic acid ligand library.

* * * * *